United States Patent
Boehmisch et al.

(10) Patent No.: US 7,324,192 B2
(45) Date of Patent: Jan. 29, 2008

(54) TEST APPARATUS AND METHOD FOR EXAMINING SHEET-LIKE COMPONENTS FOR PERFORATIONS

(75) Inventors: Mathias Boehmisch, Singen (DE); Cornelius Haas, Daisendorf (DE)

(73) Assignee: DaimlerChrysler AG, Stuttgart (DE)

(*) Notice: Subject to any disclaimer, the term of this patent is extended or adjusted under 35 U.S.C. 154(b) by 206 days.

(21) Appl. No.: 11/192,448

(22) Filed: Jul. 28, 2005

(65) Prior Publication Data
US 2006/0028640 A1 Feb. 9, 2006

(30) Foreign Application Priority Data
Aug. 3, 2004 (DE) .................. 10 2004 037 574

(51) Int. Cl.
*G01N 21/00* (2006.01)
(52) U.S. Cl. ..................... 356/237.1; 356/437
(58) Field of Classification Search ............. 356/237.1, 356/437–439, 317, 318, 417, 337–339, 341; 250/458.1–461.2
See application file for complete search history.

(56) References Cited

U.S. PATENT DOCUMENTS 4,745,276 A * 5/1988 Broicher et al. ............ 250/253
5,956,138 A * 9/1999 Slater ........................ 356/318
2002/0071122 A1* 6/2002 Kulp et al. .................. 356/437

FOREIGN PATENT DOCUMENTS

| DE | 196 23 544 | 12/1997 |
| DE | 697 04 571 T2 | 10/2001 |
| EP | 0 947 018 B1 | 10/1999 |
| JP | 63214637 | 9/1988 |
| JP | 63214637 A * | 9/1988 |

* cited by examiner

Primary Examiner—Tarifur Chowdhury
Assistant Examiner—Jonathon D Cook
(74) Attorney, Agent, or Firm—Davidson, Davidson & Kappel, LLC

(57) ABSTRACT

A test apparatus (1) is provided for examining sheet-like components (8), in particular membrane electrode assemblies for use in a fuel cell, at least in sections and preferably continuously, for perforations (7), which apparatus includes means (9) for applying a test gas (6) to one side of the sheet-like component, means (2) for emitting electromagnetic radiation (12) in a wavelength region adapted to the test gas (6), which means are arranged on that side (11) of the sheet-like component (8) which is remote from the test gas (6), and means (3, 4, 5) for detecting any electromagnetic radiation (12) which has been absorbed by the test gas (6) in a characteristic wavelength region, and a method for carrying out an examination of this type.

8 Claims, 1 Drawing Sheet

US 7,324,192 B2

TEST APPARATUS AND METHOD FOR EXAMINING SHEET-LIKE COMPONENTS FOR PERFORATIONS

Priority is claimed to German Application Serial No. DE 10 2004 037 574.7, filed Aug. 3, 2004, the entire disclosure of which is incorporated herein.

FIELD OF THE INVENTION

The invention relates to a test apparatus for examining sheet-like components for perforations and to a method for examining sheet-like components for perforations.

BACKGROUND

Sheet-like components, such as for example membranes, in particular membrane electrode assemblies, or MEAs for short, for fuel cells, are predominantly produced in continuous production processes, for example in the form of roll product, or are produced continuously by coating or plane-parallel lamination of a plurality of webs of material to one another, these webs of material themselves at least in some cases also being in the form of roll product.

In particular in the case of MEAs, it is necessary to test for perforations, in order to be able to ensure that the fuel cells which are subsequently produced therefrom will operate reliably. In this context, there are difficulties in integrating a test of this type in the continuous production process. The integration of the testing of components of this type in manufacture requires a short test time and a high reliability of the test.

A test method which is known from DE 697 04 571 T2 is based on the detection of an exothermic chemical reaction at the perforations in an MEA. To carry out the test method, this publication provides a test apparatus having two gas spaces, which can be supplied with different gases that are able to react exothermically with one another, the gas spaces being separated from one another by the MEA, which can be clamped areally between the gas spaces. After air and/or other residual gas has been displaced out of the gas spaces by means of an inert gas, the two gas spaces are filled with different gases, with the gas in one gas space being at a greater pressure than the gas in the other gas space. The gas which is under a greater pressure penetrates through the MEA at the perforations and reacts exothermically with the other gas in the presence of a catalyst. The heat which is generated is detected by means of a thermal imaging camera.

One drawback of this method is the relatively long measurement period of typically a few minutes, associated with the need to purge the gas spaces, the complicated structure of the test apparatus, which presupposes the presence of a catalyst, and the potential danger of simultaneously handling gases which react with one another, which is associated with the risk of spontaneous combustion of the membrane and therefore of sudden, complete contact between the two gases, with the possible consequence of an explosion in the case of gases which react hypergollically with one another. Furthermore, these dangers may also occur if the test apparatus is not handled correctly, for example if an excessively high pressure is set on one side of the membrane, with the result that the membrane bursts. If only small quantities of gas penetrate through the MEA at the perforations, it is also the case that only small amounts of heat will be generated, which leads to error sources on account of the low temperature differences, for example caused by the body heat of people who are present.

SUMMARY OF THE INVENTION

Therefore, it is an object of the invention to develop an improved test apparatus for examining sheet-like components for perforations, and an improved method for examining sheet-like components for perforations.

In accordance with an embodiment of the present invention, a test apparatus for examining sheet-like components for perforations is provided including a gas source, an electromagnetic radiation source, and a detector. The gas source is arranged to apply a test gas to one side of a sheet-like component. The electromagnetic radiation source is arranged on an opposite side of the sheet-like component, and emits electromagnetic radiation in a wavelength region adapted to the test gas. The detector detects electromagnetic radiation which has been absorbed by the test gas in the wavelength region.

According to another embodiment of the present invention, the test apparatus includes means for applying a test gas to one side of the sheet-like component, means for emitting electromagnetic radiation in a wavelength region adapted to the test gas, which means are arranged on that side of the sheet-like component which is remote from the test gas, and means for detecting any electromagnetic radiation which has been absorbed by the test gas in a characteristic wavelength region.

In accordance with these embodiments of the present invention, detection of characteristic absorption bands of a test gas can be carried out significantly more quickly and reliably than the locating of an exothermic chemical reaction in accordance with the prior art, in particular if the test gas emerges through a perforation into a vacuum chamber. On account of its simplicity, the test can be carried out cyclically, for example during production of individual components from roll product which can be supplied continuously, in particular in the case of a production process in which an endless roll product is produced. Furthermore, potential error sources in the prior art, for example caused by non-uniform heating, or danger sources, for example caused by the use of hazardous substances, can be avoided.

An advantageous configuration of the test apparatus according to the invention includes, as the means for applying a test gas to one side of the component, a pressure chamber, which is open on one side and can be closed off in a gastight manner with respect to the environment by the sheet-like component, which can be arranged in a holding apparatus surrounding the opening, and a test gas source, which is connected to the pressure chamber and can be controlled preferably automatically by an evaluation apparatus. The means for emitting electromagnetic radiation can include at least one radiation source, which is arranged outside the pressure chamber and emits electromagnetic radiation that includes at least one defined wavelength region parallel to and beyond the opening which can be closed off by the sheet-like component. The apparatus may further include at least one transmitted-light sensor apparatus, which is likewise arranged outside the pressure chamber, opposite the opening and the radiation source, and an evaluation apparatus, which is connected to the transmitted-light sensor apparatus, as the means for detecting electromagnetic radiation absorbed by the test gas in a characteristic wavelength region. The radiation source can be manually controllable and/or automatically controllable by the evaluation apparatus, so that electromagnetic radiation optionally is or is not emitted. A perforation is in this case detected by spectral measurement of the electromagnetic radiation emitted by the radiation source by means of the transmitted-light sensor apparatus, by virtue of part of the emitted electromagnetic radiation being absorbed by the test gas, which has escaped from the pressure chamber through the sheet-like component at the perforation, in the spectral region in which the absorption band of the test gas lies. The electromagnetic radiation, which comprises a defined wavelength region, adapted to at least one characteristic absorption band of the test gas, is reduced in the transmitted light by the spectral components which correspond to the spectral position of the absorption band. In its edge region in the region of its narrow sides, the sheet-like component is preferably pressed onto the edge of the pressure chamber surrounding the opening by means of a holding apparatus, which can be actuated either manually or automatically, preferably by the evaluation apparatus.

An advantageous configuration of the test apparatus according to the invention provides for an additional scattered-light sensor apparatus, which is likewise connected to the evaluation apparatus, to be arranged as an additional means for the detection of electromagnetic radiation absorbed by the test gas in a characteristic wavelength region, preferably perpendicularly opposite the opening which can be closed off by the sheet-like component. This scattered-light sensor apparatus is used to detect spontaneous emission of electromagnetic radiation by the test gas molecules, excited by the absorption of part of the electromagnetic radiation emitted into the test gas which escapes from the pressure chamber through the sheet-like component via the perforations. The wavelength region to which the scattered-light sensor apparatus reacts is adapted to the test gas used.

An advantageous configuration of the test apparatus according to the invention provides that the electromagnetic radiation source and/or the transmitted-light sensor apparatus and/or the scattered-light sensor apparatus is arranged such that it can move parallel to the sheet-like component for finding the position of a perforation.

Another advantageous configuration of the test apparatus according to the invention provides for the test apparatus to be arranged in a vacuum chamber and to be operated therein.

Another advantageous configuration of the test apparatus according to the invention provides that the test apparatus has two chambers, which can be separated in a gastight manner by the sheet-like component, namely the pressure chamber which can be connected to the test gas source and a reduced-pressure chamber, which can optionally be connected to a vacuum pump, the radiation source and the transmitted-light sensor apparatus, and also if appropriate the scattered-light sensor apparatus, being arranged in the reduced-pressure chamber on the detector side of the component, so that the sheet-like component does not close off the pressure chamber in a gastight manner with respect to the environment, but rather with respect to the reduced-pressure chamber.

An additional, advantageous configuration of the test apparatus according to the invention includes an additional reference sensor, arranged in part of the beam path of the radiation source, for measuring the intensity of the unattenuated electromagnetic radiation as a reference, in order to enable fluctuations in the intensity of the radiation source to be taken into account when evaluating the spectral measurement.

Another advantageous configuration of the test apparatus according to the invention provides for the radiation source to be a laser light source which emits laser light in a defined frequency band.

An additional advantageous configuration of the test apparatus according to the invention provides for the laser light source to emit a laser fan.

A particularly advantageous configuration of the test apparatus according to the invention provides for the test gas to be carbon dioxide gas.

Another advantageous configuration of the test apparatus according to the invention includes a marking apparatus, which is connected to the evaluation apparatus and can be controlled by the latter, in order, at least in sections, to mark defective areas which include perforations.

An additional advantageous configuration of the test apparatus according to the invention includes a cutting apparatus, which is connected to the evaluation apparatus and can be controlled by the latter, for removing defective areas which include perforations at least in sections.

An additional, particularly advantageous configuration of the invention provides for the test apparatus to be integrated in the production process, in which case, in the event of perforations being detected in the sheet-like component, a further treatment, removal or marking of the section which has been recognized as defective is initiated automatically.

In accordance with another embodiment of the present invention, a method is provided, comprising the steps of:

arranging the sheet-like component in a test apparatus, for example between a pressure chamber which can be connected to a test gas source and a reduced-pressure chamber which can be connected to a vacuum pump for removing residual gas or for evacuation, applying a test gas to one side of the sheet-like component, for example from the pressure chamber, emitting electromagnetic radiation in a wavelength region, which is adapted to the test gas, in particular its characteristic absorption band, onto that side of the sheet-like component which is remote from the side which is exposed to the test gas, parallel to this side, for example by emitting a laser beam, which includes a wide wavelength region, parallel to the detector side of the component, remote from the pressure chamber, spectroscopically recording the electromagnetic radiation in the transmitted light, for example by means of a transmitted-light sensor apparatus, and/or in the scattered light, for example by means of a scattered-light sensor apparatus, the term scattered light encompassing both scattered electromagnetic radiation and radiation which has been absorbed and emitted again on all sides, subtracting the electromagnetic radiation received in the transmitted light from the electromagnetic radiation emitted in the same wavelength region, and/or subtracting the electromagnetic radiation received in the scattered light from the electromagnetic radiation emitted in the same wavelength region, for example in an evaluation apparatus, which is connected to the transmitted-light sensor apparatus and/or the scattered-light sensor apparatus and if appropriate also to a reference sensor, comparing the spectral region of the result of the subtraction with the spectral position of the characteristic absorption band of the test gas in the emitted wavelength region, for example in the evaluation apparatus, and if they correspond, outputting a signal which indicates a perforation, if they do not correspond, outputting a signal which indicates that the test did not find anything, in which context the signals can be used not only merely to provide an indication, but also to carry out automatic sorting of the tested components following the examination and/or to remove the tested MEA from the test apparatus and replace it with the next MEA to be tested, removing the sheet-like component from the test apparatus.

The terms spectral measurement and spectroscopic recording are also to be understood, in the context of the present invention, as encompassing measurement of the integral light intensity in selected wavelength regions.

An advantageous configuration of the method according to the invention provides that the application of a test gas to one side of the sheet-like component takes place at a superatmospheric pressure.

Another advantageous configuration of the method according to the invention includes the method step of automatically inserting and/or automatically removing the sheet-like component into/from the test apparatus.

A particularly advantageous configuration of the method according to the invention includes the method step of tracing the position of the perforation by relative movement of the electromagnetic radiation source and of the receiver parallel to the sheet-like component.

BRIEF DESCRIPTION OF THE DRAWING

An exemplary embodiment of the invention is illustrated in the drawing in accordance with FIG. 1, which shows a side view of a schematic structure of a test apparatus according to the invention, which is explained in more detail below.

DETAILED DESCRIPTION

Figure 1:
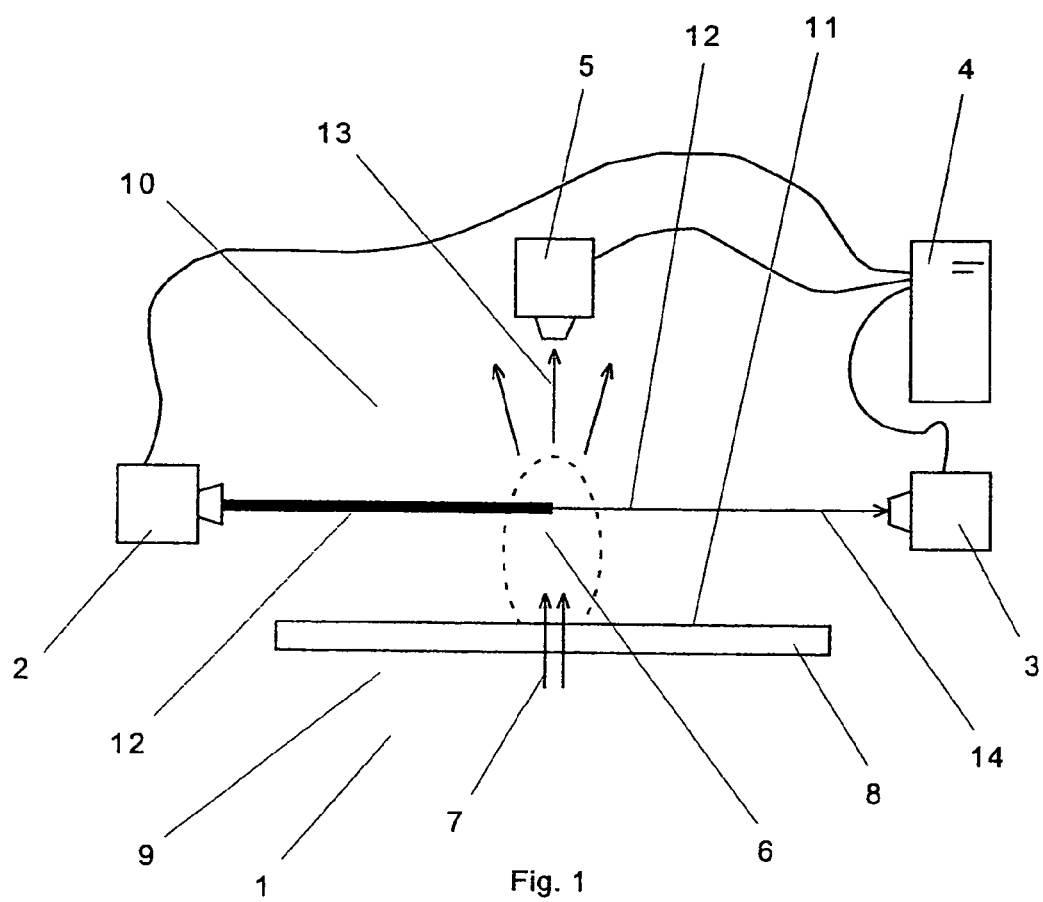

A test apparatus 1 according to an embodiment of the invention substantially comprises a laser source 2, a transmitted-light sensor 3 and a computer 4 connected to the transmitted-light sensor 3. In addition, the computer 4 is connected to the laser source 2 in order to control the latter in accordance with the test operation. In addition to the transmitted-light sensor 3, a scattered-light sensor 5, which is connected to the computer 4, is arranged between laser source 2 and transmitted-light sensor 3, perpendicular to the main direction of radiation 14. The computer 4 serves as the evaluation apparatus for determining whether test gas 6 is passing through perforations 7 in the membrane electrode assembly (MEA) 8 onto the detector side 11 facing the laser light source 2 and the sensors 3 and 5, and as a control unit for the test operation, and is also able to influence the production process for the MEA 8.

A core concept of the invention is the detection of perforations 7 or holes in sheet-like components, such as for example an MEA 8, by means of absorption spectroscopy. Two chambers 9 and 10, which are separated in an inherently gastight manner by the component and at least one of which can be supplied with a test gas 6, are only connected to one another at a perforation 7 or at locations where there is a hole. As a result of a slightly greater pressure prevailing in the pressure chamber 9 to which the test gas 6 can be supplied, a test gas 6, which is a gas or a gas mixture with defined properties, flows through the leaks at the perforations 7 into the other chamber, namely the reduced-pressure chamber 10. One significant property of the test gas 6 is that it absorbs electromagnetic radiation in a defined wavelength region, such as for example the laser beam 12 emitted by the laser source 2. On the detector side 11 of the component, corresponding to the detector side 11 remote from the pressure chamber 9, an electromagnetic radiation source 2 emits electromagnetic radiation 12, the wavelength region of the electromagnetic radiation being selected in such a way that at least one absorption band of the test gas 6, preferably a characteristic absorption band, lies within the wavelength region. Test gas 6 which passes through the perforations 7 into the reduced-pressure chamber 10 selectively absorbs part of the electromagnetic radiation 12 in the wavelength region of this absorption band, which can be measured by a suitably arranged transmitted-light sensor 3. A further reference sensor, as reference, can measure an unattenuated part-beam of the radiation source 2 in order to enable fluctuations in the intensity of the radiation source 2 to be taken into account. Since the test gas 6 itself, having been excited by the absorbed part of the radiation, can in turn emit non-directional electromagnetic radiation 13 on all sides, for example through fluorescence, it is also conceivable for the presence of the test gas 6 in the reduced-pressure chamber 10 to be determined by detection of this radiation 13. This radiation 13 can be detected using a scattered-light sensor 5, which is preferably arranged perpendicular to the main direction of radiation 14, in which case, with the exception of the main direction of radiation 14, any desired position of the scattered-light sensor 5 with respect to the beam path of the radiation source 2 is conceivable, since the radiation 14 emitted by the test gas 6 is on all sides and non-directional. Furthermore, it is also conceivable to use the scattered-light sensor 5 to detect radiation which has been scattered at the test gas 6, for example through refraction and reflection. A variant of the structure of the test apparatus 1 which has been specifically adapted to continuously produced sheet-like components to be examined is targeted, local excitation of the test gas 6, for example by means of a laser beam 12, combined with a relative movement between component and excitation source/sensor apparatuses. A linear arrangement is also possible, in which case a larger area of the component can be tested simultaneously. A combination of these options is also possible.

A typical application for the test apparatus is, for example, the testing of fuel cell components, in particular MEAs or bipolar plates, or the sub-components thereof, for example the membranes thereof. Use both in the production process and for incoming goods inspection are conceivable. Other conceivable applications include, for example, the testing of films or foils for pinholes, or of other electrodes, for example for batteries. Furthermore, a combination of the test apparatus according to the invention with additional recording of a thermal image of an exothermic chemical reaction, occurring at a perforation, between two reactive gases which are otherwise separated by the component, is conceivable.

What is claimed is:

1. A test apparatus for examining sheet-like components for perforations, comprising:
   a pressure chamber, which is open on one side and can be sealed in a gastight manner by a sheet-like component;
   a controllable test gas source connected to the pressure chamber;
   at least one radiation source arranged outside the pressure chamber, the at least one radiation source emitting electromagnetic radiation, in a beam path parallel to and beyond the opening, that includes at least one defined wavelength region;
   at least one transmitted-light sensor arranged outside the pressure chamber, and opposite the opening and the radiation source; and
   an evaluation apparatus connected to the transmitted-light sensor apparatus, the radiation source being manually controllable and/or automatically controllable by the evaluation apparatus;

wherein at least one of the electromagnetic radiation source, the transmitted-light sensor apparatus, and the scattered-light sensor apparatus is movable parallel to the sheet-like component.

2. A test apparatus for examining sheet-like components for perforations, comprising:
a pressure chamber, which is open on one side and can be sealed in a gastight manner by a sheet-like component;
a controllable test gas source connected to the pressure chamber;
at least one radiation source arranged outside the pressure chamber, the at least one radiation source emitting electromagnetic radiation, in a beam path parallel to and beyond the opening, that includes at least one defined wavelength region;
at least one transmitted-light sensor arranged outside the pressure chamber, and opposite the opening and the radiation source; and
an evaluation apparatus connected to the transmitted-light sensor apparatus, the radiation source being manually controllable and/or automatically controllable by the evaluation apparatus;
wherein the test apparatus is arranged in a vacuum chamber.

3. A test apparatus for examining sheet-like components for perforations, comprising:
a pressure chamber, which is open on one side and can be sealed in a gastight manner by a sheet-like component;
a controllable test gas source connected to the pressure chamber;
at least one radiation source arranged outside the pressure chamber, the at least one radiation source emitting electromagnetic radiation, in a beam path parallel to and beyond the opening, that includes at least one defined wavelength region;
at least one transmitted-light sensor arranged outside the pressure chamber, and opposite the opening and the radiation source;
an evaluation apparatus connected to the transmitted-light sensor apparatus, the radiation source being manually controllable and/or automatically controllable by the evaluation apparatus; and
a second chamber;
wherein the pressure chamber and the second chamber can be separated in a gastight manner by the sheet-like component, the second chamber having a reduced pressure in comparison to the pressure chamber, the radiation source and the transmitted-light sensor apparatus arranged in the second chamber.

4. The test apparatus as claimed in claim 3, wherein a vacuum pump is connected to the second chamber.

5. A test apparatus for examining sheet-like components for perforations, comprising:
a pressure chamber, which is open on one side and can be sealed in a gastight manner by a sheet-like component;
a controllable test gas source connected to the pressure chamber;
at least one radiation source arranged outside the pressure chamber, the at least one radiation source emitting electromagnetic radiation, in a beam path parallel to and beyond the opening, that includes at least one defined wavelength region;
at least one transmitted-light sensor arranged outside the pressure chamber, and opposite the opening and the radiation source;
an evaluation apparatus connected to the transmitted-light sensor apparatus, the radiation source being manually controllable and/or automatically controllable by the evaluation apparatus;
a scattered-light sensor apparatus, connected to the evaluation apparatus; and
a second chamber;
wherein the pressure chamber and the second chamber can be separated in a gastight manner by the sheet-like component, the second chamber having a reduced pressure in comparison to the pressure chamber, the radiation source, the scattered-light sensor apparatus, and the transmitted-light sensor apparatus arranged in the second chamber.

6. The test apparatus as claimed in claim 5, wherein a vacuum pump is connected to the second chamber.

7. A test apparatus for examining sheet-like components for perforations, comprising:
a pressure chamber, which is open on one side and can be sealed in a gastight manner by a sheet-like component;
a controllable test gas source connected to the pressure chamber;
at least one radiation source arranged outside the pressure chamber, the at least one radiation source emitting electromagnetic radiation, in a beam path parallel to and beyond the opening, that includes at least one defined wavelength region;
at least one transmitted-light sensor arranged outside the pressure chamber, and opposite the opening and the radiation source; and
an evaluation apparatus connected to the transmitted-light sensor apparatus, the radiation source being manually controllable and/or automatically controllable by the evaluation apparatus;
further comprising a cutting apparatus, wherein the cutting apparatus is connected to, and controlled by, the evaluation apparatus.

8. A method for examining sheet-like components for perforations comprising the steps of:
arranging a sheet-like component in a test apparatus;
applying a test gas to one side of the sheet-like component;
emitting electromagnetic radiation in a wavelength region which is adapted to the test gas onto an opposing side of the sheet-like component, parallel to the opposing side;
spectroscopically recording electromagnetic radiation in the transmitted light and/or in the scattered light;
subtracting the electromagnetic radiation received in the transmitted light from the electromagnetic radiation emitted in the wavelength region; and/or
subtracting the electromagnetic radiation received in the scattered light from the electromagnetic radiation emitted in the wavelength region;
comparing a spectral region of the result of the subtraction with a spectral position of a characteristic absorption band of the test gas in the wavelength region;
and if they correspond, outputting a signal which indicates a perforation;
if they do not correspond, outputting a signal which indicates that the test did not detect a perforation;
removing the sheet-like component from the test apparatus;
tracing a position of a detected perforation by moving a source of the emitted electromagnetic radiation and the sensor(s) for spectroscopically recording electromagnetic radiation in the transmitted light and/or in the scattered light, parallel to the sheet-like component.

* * * * *